United States Patent
Sexton

[11] Patent Number: 6,085,027
[45] Date of Patent: Jul. 4, 2000

[54] CIGARETTE LIGHTER AROMATIC DISPENSER

[76] Inventor: Vanessa L. Sexton, 23522 Flo St., Warren, Mich. 48091

[21] Appl. No.: 09/135,328

[22] Filed: Aug. 17, 1998

[51] Int. Cl.[7] .............................. A61H 33/12; B60L 1/02
[52] U.S. Cl. ........................................... 392/404; 219/202
[58] Field of Search ..................... 392/386, 390, 392/394, 395, 403, 404; 219/202; 131/187, 188, 189; 239/44, 45, 57

[56] References Cited

U.S. PATENT DOCUMENTS

| | | | |
|---|---|---|---|
| 3,006,042 | 10/1961 | Calandra | 392/386 |
| 3,551,092 | 12/1970 | Masson | 392/386 |
| 4,686,353 | 8/1987 | Spector | 219/275 |
| 4,692,590 | 9/1987 | Spector | 219/275 |
| 4,731,521 | 3/1988 | Spector et al. | 219/274 |
| 5,373,581 | 12/1994 | Smith | 392/390 |
| 5,394,506 | 2/1995 | Stein et al. | 392/390 |
| 5,432,882 | 7/1995 | Glynn | 392/392 |
| 5,710,406 | 1/1998 | Garris et al. | 392/386 |

Primary Examiner—Sang Paik
Attorney, Agent, or Firm—Henderson & Sturm LLP

[57] ABSTRACT

A cigarette lighter aromatic dispenser 10 including a cylindrical heater body member 20 provided with an interior stepped shoulder 21 dimensioned to receive a portion of a receptacle member 30 containing a heat activated aromatic material 35. The exterior of the heater body member 20 is threadedly engaged with a portion of an enlarged actuator knob member 40 provided with a plurality of vertically aligned spaced rods 42.

3 Claims, 1 Drawing Sheet

CIGARETTE LIGHTER AROMATIC DISPENSER

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of car air freshening systems in general, and in particular to cigarette lighter charged air fresheners.

2. Description of Related Art

As can be seen by reference to the following U.S. Pat. Nos. 4,686,353; 4,692,590; 4,731,521; and 5,432,882, the prior art is replete with myriad and diverse cigarette lighter charged air freshener devices.

While all of the aforementioned prior art constructions are more than adequate for the basic purpose and function for which they have been specifically designed, they are uniformly deficient with respect to their failure to provide a simple, efficient, and practical actuator knob arrangement that is specifically designed to dissipate heat, prevent the user's fingers from contacting the aroma generating substance, enhance the user's grasp while pushing and pulling on the actuator knob, and also providing an aesthetically pleasing appearance that will not detract from the general appearance of the vehicle interior.

As a consequence of the foregoing situation, there has existed a longstanding need for a new and improved cigarette lighter aromatic dispenser that will overcome all of the stated deficiencies that are to be found in the prior art construction, and the provision of such a construction is a stated objective of the present invention.

BRIEF SUMMARY OF THE INVENTION

Briefly stated, the cigarette lighter aromatic dispense that forms the basis of the present invention comprises in general, a heater unit, an aroma dispensing unit, and an actuator knob unit wherein the actuator knob unit captively engages the aroma dispensing unit relative to the heater unit.

As will be explained in greater detail further on in the specification, the heater unit compresses a heater body member having an interior heating coil operatively connected to a cigarette plug adapter element disposed on one end of the body member wherein the other end of the body member is dimensioned to receive the aroma dispensing unit in a generally snap fit fashion.

In addition, the actuator knob unit compresses an enlarged actuator knob member dimensioned to threadably engage the exterior of the heater body member to captively engage the aroma dispensing unit intermediate the actuator knob member and the heater body member.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein.

DETAILED DESCRIPTION OF THE INVENTION

Figure 1:
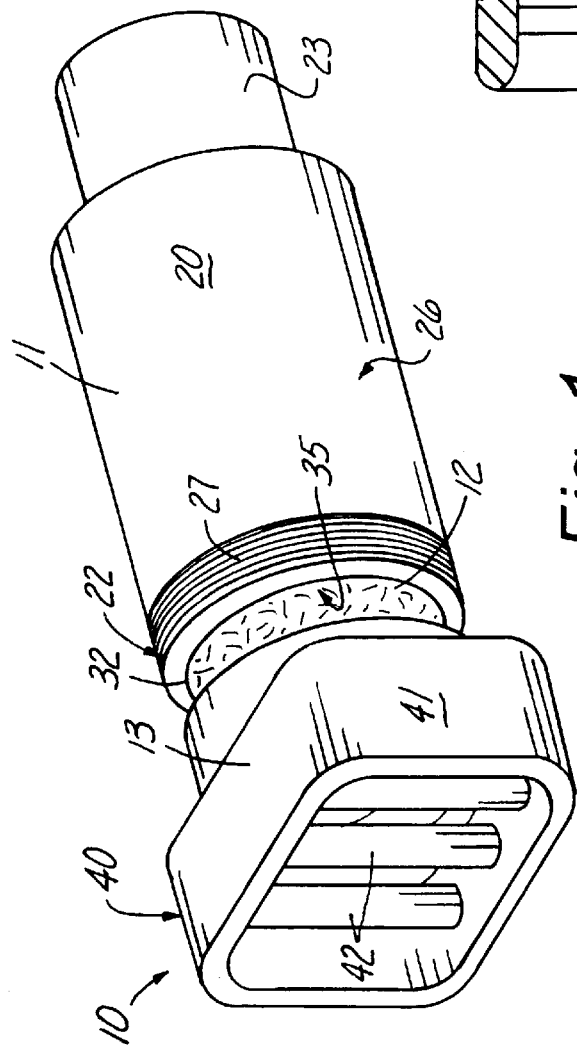
FIG. 1 is a partially exploded perspective view of the cigarette lighter aromatic dispenser that forms the basis of the present invention.

As can be seen by reference to the drawings, and in particularly to FIG. 1, the cigarette lighter aromatic dispenser that forms the basis of the present invention is designated generally by the reference number 10. The aromatic dispenser 10 comprises in general, a heater unit 11, an aroma dispensing unit 12, and an actuator knob unit 13. These units will now be described in seriatim fashion.

Figure 3:
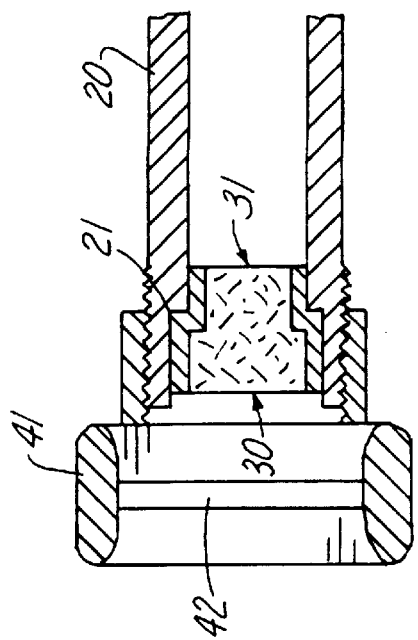
FIG. 3 is a cross-sectional detail view showing the operative engagement between the heater unit, the aroma dispensing unit, and the actuator knob unit.
Figure 2:
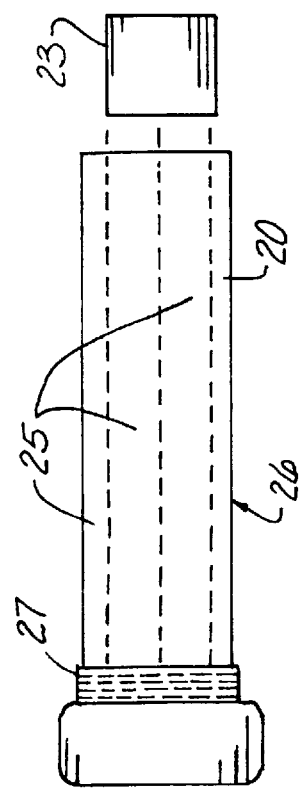
FIG. 2 is a side plan view of the aromatic dispenser.

As shown in FIGS. 1 through 3, the heater unit 11 comprises a generally hollow cylindrical heater body member 20 having an interior stepped shoulder 21 formed on the outboard end 22, and a cigarette plug adapter element 23 formed on the inboard end 24. The adapter element 23 is operatively connected to a conventional cigarette lighter heating coil 25 disposed in the interior of the intermediate portion 26 of the heater body member 20.

In addition, the exterior of the outboard end 22 of the heater body member 20 is threaded as at 27 for reasons that will be explained in greater detail further on in the specification.

As can also be seen by reference to FIGS. 1 through 3, the aroma dispenser unit 12 comprises a stepped shoulder receptacle member 30 having a reduced diameter interior portion 31 which is dimensioned to be received in the outboard end 22 of the heater body member 20 and an enlarged diameter exterior portion 32 which is dimensioned to rest against the outboard end 22 of the heater body member 20 in a generally flush fashion. The interior of the receptacle member 30 is dimensioned to receive a quantity of heat activated aromatic material 35 such as an aromatic gel, potpourri, or the like.

Still referring to FIGS. 1 through 3, it can be seen that the actuator knob unit 13 comprises an enlarged actuator knob member 40 having a generally hollow rectangular outer finger grip portion 41 wherein the interior of the finger grip portion 41 is provided with a plurality of vertically aligned spaced rods 42 whose purpose and function will be described presently.

As can best be seen by reference to FIGS. 2 and 3, the actuator knob member 40 is also provided with a generally cylindrical interiorly threaded collar portion 42 which extends rearwardly from the finger grip portion 41 and which is adapted to threadably engage the outboard end 22 of the heater body member 20 in a well recognized fashion to captively engage the aromatic dispenser unit 12 intermediate the heater unit 11 and the actuator knob unit 13.

By now it should be appreciated that not only does the enlarged actuator knob member 40 provide an easily grasped actuator surface for the pushing and pulling motion required to engage and disengage the aromatic dispenser 10 with a conventional vehicle cigarette lighter outlet (not shown), but the actuator knob surface serves to dissipate heat generated by the interior heating coil 25. The vertically aligned spaced rods 42 prevent the user's fingers from coming into contact with the heat activated aromatic material 35.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

I claim:

1. A cigarette lighter aromatic dispenser for use with a conventional vehicle cigarette lighter socket wherein the aromatic dispenser consists of:

a heater unit including an elongated cylindrical body member having an outer end, an inner end, and an intermediate portion; wherein the inner end is provided with a cigarette plug adapter element that is operatively associated with a heater element disposed in the interior of the cylindrical body member;

an aroma dispensing unit including a receptacle member dimensioned to be received in the outer end of the cylindrical body member wherein said outer end of the cylindrical body member is provided with an interior stepped shoulder and at least a portion of the receptacle member is dimensioned to be received in said stepped shoulder; and an actuator knob unit including an enlarged actuator knob member having an enlarged generally hollow rectangular outer finger grip portion provided with a plurality of vertically aligned spaced rods extending across the interior of the finger grip portion; and, having a rearwardly extending collar portion that is operatively engaged with the outer end of the cylindrical body member; whereby, the aroma dispensing unit is captively engaged intermediate the heater unit and the actuator knob unit.

2. The dispenser as in claim 1 wherein the aroma dispensing unit further includes:

a quality of heat activated aromatic material disposed within said receptacle member.

3. The dispenser as in claim 2 wherein both the exterior of the outer end of the cylindrical body member and the interior of the collar portion of the actuator member are threadedly engaged with one another.

* * * * *